(12) United States Patent
Walther

(10) Patent No.: US 7,134,591 B2
(45) Date of Patent: Nov. 14, 2006

(54) METHOD OF AND APPARATUS FOR TESTING A WIRE BOND CONNECTION

(75) Inventor: Frank Walther, Brakel (DE)

(73) Assignee: Hesse & Knipps GmbH, Paderborn (DE)

( * ) Notice: Subject to any disclaimer, the term of this patent is extended or adjusted under 35 U.S.C. 154(b) by 0 days.

(21) Appl. No.: 10/818,466

(22) Filed: Apr. 2, 2004

(65) Prior Publication Data
US 2004/0226983 A1    Nov. 18, 2004

(30) Foreign Application Priority Data
Apr. 4, 2003    (DE)    ................. 103 15 639

(51) Int. Cl.
*B23K 31/12* (2006.01)
*B23K 31/02* (2006.01)
*G01N 3/08* (2006.01)

(52) U.S. Cl. .................. 228/104; 228/180.5; 73/827

(58) Field of Classification Search ............ 228/4.5, 228/102–103, 180.5; 73/827, 831
See application file for complete search history.

(56) References Cited

U.S. PATENT DOCUMENTS

| 3,890,831 | A |   | 6/1975 | Cusick et al |
| 4,040,885 | A | * | 8/1977 | Hight et al. ................. 156/378 |
| 4,422,568 | A | * | 12/1983 | Elles et al. ................... 228/111 |
| 4,907,458 | A | * | 3/1990 | Biggs et al. ................... 73/827 |
| 5,085,084 | A | * | 2/1992 | Salatino ....................... 73/827 |
| 5,195,237 | A | * | 3/1993 | Cray et al. .................... 29/838 |
| 5,591,920 | A |   | 1/1997 | Price et al. |
| 5,894,981 | A | * | 4/1999 | Kelly ........................ 228/104 |
| 6,230,569 | B1| * | 5/2001 | Ball ............................ 73/827 |
| 6,341,530 | B1| * | 1/2002 | Sykes .......................... 73/831 |
| 6,564,115 | B1|   | 5/2003 | Kinnaird |
| 2002/0040921 | A1 |   | 4/2002 | Ball et al |
| 2002/0043109 | A1 | * | 4/2002 | Siu ............................. 73/643 |
| 2004/0079790 | A1 | * | 4/2004 | Mayer et al. ............. 228/180.5 |

FOREIGN PATENT DOCUMENTS

| DE | 38 10 929 | 10/1988 |
| DE | 37 17 856 | 12/1988 |
| DE | 197 52 319 | 5/1998 |
| DE | 10394754 | 5/2004 |
| JP | 01-288752 A | * 11/1989 |

* cited by examiner

*Primary Examiner*—Lynne R. Edmondson
(74) *Attorney, Agent, or Firm*—Andrew Wilford

(57) ABSTRACT

A method and apparatus for the nondestructive testing of a bond connection between a bond wire and a substrate or pad which utilizes an ultrasonic tool for bonding the bond wire to the substrate or pad. The test force is applied in the plane of the bond connection transversely to the bond wire through an ultrasonic welding tool.

10 Claims, 1 Drawing Sheet

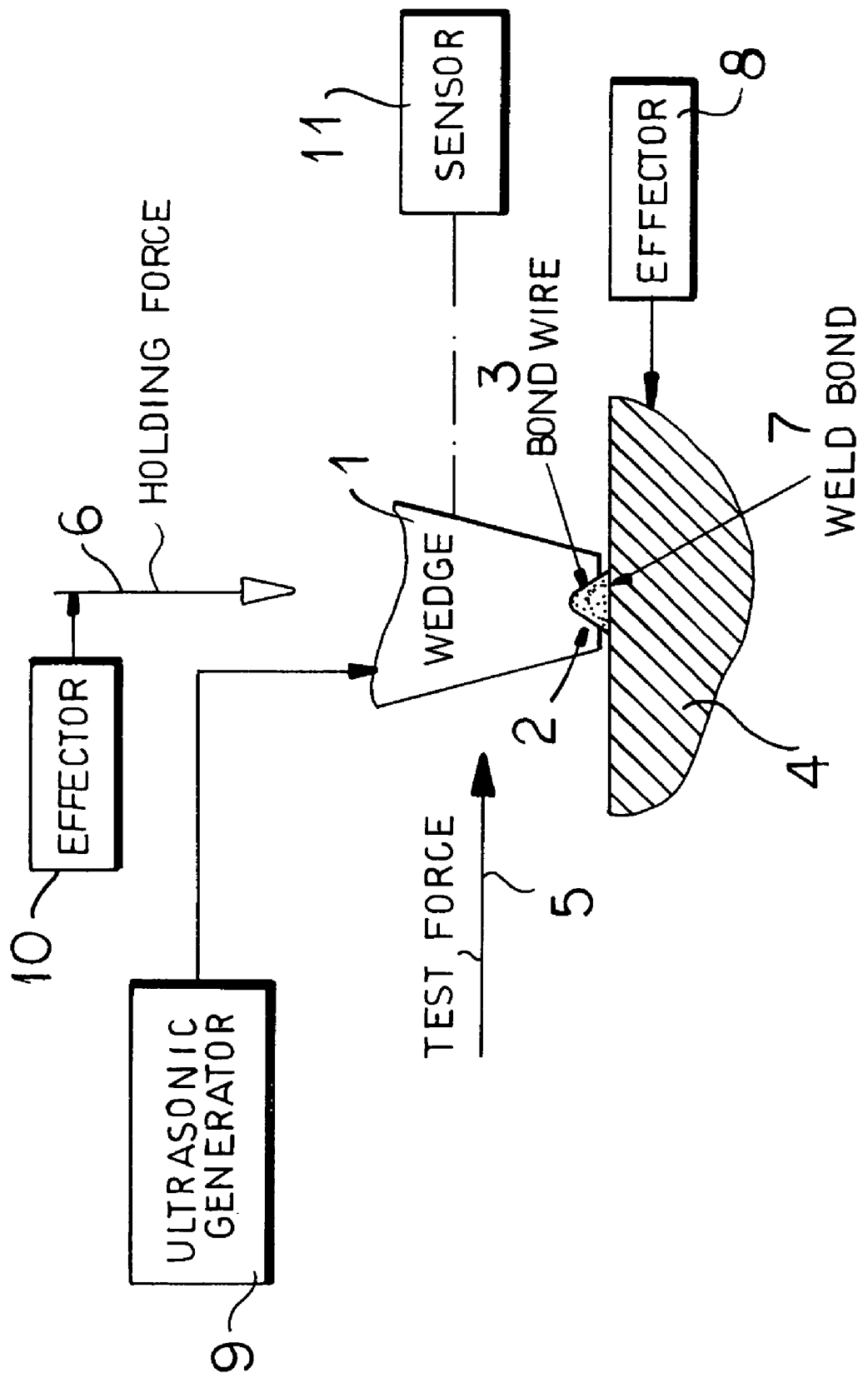

METHOD OF AND APPARATUS FOR TESTING A WIRE BOND CONNECTION

FIELD OF THE INVENTION

My present invention relates to a method of and to an apparatus for testing a wire bond connection. More particularly, the invention relates to wire bond fabrication and to a method for the nondestructive testing of a wire bond formed by ultrasonic means between a wire, usually referred to as a bond wire, and a substrate or bond pad.

The invention also relates to an apparatus for producing a wire bond connection and for nondestructively testing the connection made between the bond wire and the substrate by means of an ultrasonic tool.

BACKGROUND OF THE INVENTION

Various processes for testing the quality of a wire bond connection have been proposed heretofore. For example, the bond connection formed between the bond wire and the substrate can be tested by applying in the longitudinal direction of the wire a force thereto which ruptures the bond between the bond wire and the substrate. The force which is detected in this test is that which is required to destroy the bond connection. While this method does supply information as to the quality of the bond connection, it has the drawback that the use of the method destroys the bond connection itself which is a significant drawback. The nondestructive tension testing method applies force in the longitudinal direction of the bond wire while a satisfactory bond connection can resist the force so that only defective bond connections will be destroyed. Connections which satisfy this type of qualitative test can be used.

Quality testing of the connection between bond wires and their substrates of the state of the art have the drawback that to apply the test force, a device must be provided on the bond head which allow clamping to the wire. Usually the wire clamp has two jaws which must engage the wire between them so that a pull can be exerted on the wire through the clamp. Aside from the fact that the construction of the clamp is expensive, the use of the clamp takes a considerable amount of time and testing with these devices thus may slow down the rate of production of bond-wire connection.

OBJECTS OF THE INVENTION

It is, therefore, the principal object of the present invention to provide a method of nondestructively testing the connections between bond wires and their substrates whereby the drawbacks of the earlier systems can be avoided.

Another object of this invention is to provide a method for the nondestructive testing of such bond wire connections which eliminates the need for expensive devices to grip the bond wire and which enables qualitative testing to be carried out within a much shorter time than has been the case heretofore, and indeed the shortest possible time.

It is also an object of this invention to provide an apparatus which can effect nondestructive qualitative testing of such bond connections at low cost and within the shortest possible time period.

SUMMARY OF THE INVENTION

These objects and others which will become apparent hereinafter are attained, in accordance with the invention in a method and with an apparatus whereby the testing force is applied to the wire by the ultrasonic tool itself.

According to the method aspect of the invention, therefore, an ultrasonic tool is pressed against a bond wire which can be engaged in a seat of the tool receiving the bond wire and is pressed by that tool against a substrate and an ultrasonic signal is applied to the tool to ultrasonically weld the bond wire to the substrate. Using the tool, a test force is applied to the bond wire, which has been ultrasonically welded to the substrate by the use of that tool.

By contrast with the art-recognized prior techniques which have been used, the invention has the significant advantage that no additional construction is required which is equivalent to a wire clamp on the bond head and thus a damage to the bond connection during the test by the connection of the bond clamp can be avoided or excluded.

The testing force, which can be applied directly to the location of the bond connection is preferably transverse to the wire direction and is applied to the wire or the bond connection and the failure of the bond can be immediately indicated by a relative movement between the seat of the transducer or ultrasonic tool and the substrate or between the wire and the substrate.

In this manner the bond is subjected not only to a quality testing of the bond itself but is additionally subjected to a shear test and particularly a nondestructive shear test. The bond connection is loaded by the test force which is especially a transverse or shear force, the bond connection normally being sufficient to withstand this test force if the bond connection is to be considered as having passed the test.

It thus is possible to avoid breakage of a satisfactory bond connection during the test process. Only bond connections which do not pass the qualitative testing can be damaged by a correspondingly selected force and thus these cannot be used in any event. It is especially advantageous that the method and apparatus for making a wire bond connection between the bond wire and a substrate utilize an ultrasonic tool in which the test force is applied to the ultrasonic tool itself, that is in so-called wedge bonding, by the wedge itself.

For this apparatus, for example, following the formation of a wire bond connection, the wedge can be lifted from the bond wire and positioned alongside the bond wire so that a lateral movement of the transducer suspension, i.e. the suspension for the ultrasonic tool, transverse to the longitudinal direction of the wire will suffice to signal a defective wire bond connection. If the bond connection withstands the force applied laterally by the tool to the wire, it is considered to have passed the qualitative test. In this case the ultrasonic tool functions similar to a shear wedge.

In an especially advantageous embodiment of the invention the test force can be applied to the wire while the wire is engaged in a groove in the tip of the ultrasonic tool and/or the tool is still in engagement with the bond wire in the position in which the bond connection was made. This is the important advantage that after producing the bond connection, the ultrasonic tool need not be lifted from the bond connection or repositioned with respect to it for the test. In addition, because the tool remains in engagement with the bond wire after the bond or connection has been made, there is an optimum form-fitting connection between the ultrasonic tool and the bond wire or the bond connection to enable the test to be made. A force can be provided directly orthogonal to the bond direction in the bond plane by pressing the substrate relative to the tool with a force parallel to the bond plane and perpendicular to the bond wire to test whether the bond connection is satisfactory. As a result, no damage to the wire or bond connection can occur unless the bond connection fails. The force is preferably applied by the ultrasonic tool through one of the lateral wall regions of the groove in the tip of the tool.

Naturally, to prevent the lateral application of a force from camming the ultrasonic tool away from the bond wire by reason of the fact that the walls of the groove are inclined to the angle, e.g. form an angle of about 70° between them, sufficient force must be applied to hold the tool against the bond wire.

This test method has the important advantage over prior art systems that the cost of the apparatus for testing the bond strength is significantly lower since the ultrasonic tool forms the testing element according to the invention and additional wire clamps, as are required by the prior art systems, are not necessary. The testing time for carrying out the test process according to the invention is significantly less since separate control and operations relating to test elements, including the clamping step, can be avoided.

In prior art techniques, it was first necessary to clamp the bond wire in a clamping device and subsequently remove the clamp after the test force had been removed. These steps in the cycle are completely eliminated since the use of the tool for the testing of the bond enables the test to be carried out in the shortest possible time.

The testing force can require that the bond head or the tool (ultrasonic transducer) or both be movable transversely to the wire direction and it is possible to effect that displacement which is necessary by automatically shifting the tip of the tool within the spring stiffness of the tool to sufficiently load the bond connection and thus determine the quality of the bond. Of course the substrate can be moved instead or as well and the test force and/or test movement can be detected in the bond head or by the reaction force at the substrate or in the movement axes of the bonding machine and/or the holder for the substrate or for the tool. All that is necessary is that a force be developed between the tip of the ultrasonic tool and the wire or the substrate and thus both the movement and the measurement can be effected via the table upon the substrate, mounted, for example, through an effector which acts upon that table or a sensor which responds to the force applied to the substrate through the bond connection.

The quality of the bond connection can be determined by at least one of the following steps:

i) A predetermined testing force is applied and the resulting movement of the ultrasonic tool is detected and evaluated.

ii) Alternatively or in combination, a test force is applied and the reaction force is detected and evaluated.

iii) In an alternative or further feature a movement of the receptacle in the ultrasonic tool in which the bond wire is seated is induced and the reaction force (through the bond wire, bond connection and substrate) is detected and evaluated.

iv) A movement of the ultrasonic tool can be initiated and a deformation of the wire and/or of the bond connection and/or of the ultrasonic tool or the tool holder can be detected by means of a sensor and evaluated to provide an indication of the bond strength.

This latter step can be carried out with a relatively simple apparatus, namely, the apparatus for producing the bond to give a quality indication thereof. In that case, a sensor directly and/or indirectly measuring the force upon the ultrasonic tool while it engages the wire or is coupled thereto so that the force corresponds to the force on the bond wire or the bond connection, or which detects a movement of the ultrasonic tool is all that is required to be added to the existing bonding head.

If desired, a force sensor can be provided on the bonding head which measures the force which is applied to the bond wire through the ultrasonic tool. The measured force can serve as a control parameter which enables the axis of the bonding machine to be so controlled that a desired test force is applied. If the bond breaks at this force, as can be determined by a position sensor, a failure is noted. Exceeding a predetermined threshold at the position sensor can indicate a damaged bond and a damaged or ineffective bond can also be indicated by the failure to achieve a setpoint force.

BRIEF DESCRIPTION OF THE DRAWING

The above and other objects, features, and advantages will become more readily apparent from the following description, reference being made to the sole FIGURE which is a diagram showing an ultrasonic welding tool is applied to the present invention.

SPECIFIC DESCRIPTION

In the drawing I have shown a substrate 4 to which a bond wire 3 is to be ultrasonically welded and which can be mounted on a table displaceably by an effector 8, if desired, as one way of generating the test force described in greater detail hereinafter. The ultrasonic tool is here a wedge 1, which also may be an ultrasonic transducer or which is connected to an ultrasonic transducer or source represented as the ultrasonic generator 9, and has a V-shaped groove 2 which engages the bond wire 3 and presses with a holding force 6 against the substrate 4.

After the wire bond welding operation, a welding bond 7 is formed between the bond wire and the substrate 4 which is to be tested in accordance with the invention. In the bond operation the bond wire 3 deformed by the bonding operation is completely enclosed by the V-shaped groove 2.

To carry out the quality testing during the fabrication of a bond connection between the bond wire and the substrate 4 or bond pad, formed by the friction welding produced by the ultrasonic action, a test force is applied to the bond wire 3 or the wire bond connection in the direction of the arrow 5, transverse to the longitudinal axis of the bond wire which runs perpendicular to the plane of the paper in the drawing.

Because the bond wire 3 is trapped in the V-shaped groove, whose flanks include an angle of 70° with one another in a preferred embodiment of the invention, that test force if applied by the wedge 1 or the effector 8, is in effect a shear force at the weld bond 7. The holding force 6 must be sufficient to prevent the wedge 1 from being cammed out of engagement with the bond wire 3 by the test force during the test. To apply the test force, various techniques can be used including the use of an effector 8 acting upon the table carrying the substrate. Other techniques can be used including the use of an effector 8 acting upon the table carrying the substrate, other techniques can use an effector 10 acting upon the bond head and applied via the stiffness of the ultrasonic tool 1 to the bond wire 3. An effector can also act upon the tool 1 so as to bias it pivotally against the bond wire 3 in the transverse direction.

In any case, the force is applied between the bond wire and the substrate 4 transversely to the bond wire and while it is trapped in the V-shaped groove 2.

The quality of the bond is determined by whether the bond is capable of withstanding a certain test force as measured, for example, by a sensor 11. If the connection between the bond wire 3 and the substrate 4 does not resist the force, as can be determined by a sudden reduction of the reaction force or a sudden displacement of the tool, a rupture of the bond connection is recognized.

I claim:

1. A method of making a wire bond connection and for the nondestructive testing of the wire bond connection which comprises the steps of:
   (a) forming an ultrasonic bond connection between a bond wire and a bond pad substrate by applying an ultrasonic tool against the bond wire and pressing the bond wire against the pad;
   (b) after forming said ultrasonic bond connection, testing the ultrasonic bond connection formed in step (a) by applying a test force insufficient to break said connection to the bond wire with the ultrasonic tool; and
   c) determining a response of the bond connection to said test force, whereby the test force is applied by the same tool used for making the bond connection.

2. The method defined in claim 1 wherein the test force is applied transversely to the bond wire.

3. The method defined in claim 2 wherein the test force is applied transversely to the bond wire at the location at which the bond connection is formed.

4. The method defined in claim 3 wherein the tool is formed with a groove engaging the bond wire and the test force is applied while the bond wire is received in said tool.

5. The method defined in claim 3 wherein the test force is selected so that a satisfactory bond connection withstands the test force.

6. The method defined in claim 3 wherein the test force is applied by displacing said tool or a bonding head carrying said tool transversely to said bond wire.

7. The method defined in claim 3 wherein the response of said bond connection to said test force is determined by detecting a movement of the tool upon application of said test force.

8. The method defined in claim 3 wherein the response of said bond connection to said test force is determined by detecting a reaction force on said tool and evaluating said reaction force.

9. The method defined in claim 3 wherein the response of said bond connection is determined by detecting a deformation of said wire or of said bond connection or of said tool in response to said test force.

10. The method defined in claim 3 wherein the response of said bond connection to said test force is determined by measuring said test force or a test movement produced thereby or detected in the bonding head or in movement axes of an optical machine or in a support for said substrate.

* * * * *